United States Patent
Herrmann

(10) Patent No.: US 10,377,965 B2
(45) Date of Patent: Aug. 13, 2019

(54) PHOTOLABILE ACETAL AND KETAL COMPOUNDS FOR THE CONTROLLED RELEASE OF ACTIVE VOLATILE CARBONYL COMPOUNDS

(71) Applicant: Firmenich SA, Geneva (CH)

(72) Inventor: Andreas Herrmann, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 15/545,231

(22) PCT Filed: Jan. 19, 2016

(86) PCT No.: PCT/EP2016/050964
§ 371 (c)(1),
(2) Date: Jul. 20, 2017

(87) PCT Pub. No.: WO2016/116420
PCT Pub. Date: Jul. 28, 2016

(65) Prior Publication Data
US 2018/0010064 A1    Jan. 11, 2018

(30) Foreign Application Priority Data
Jan. 21, 2015 (EP) .................... 15151980

(51) Int. Cl.
*C07D 319/08* (2006.01)
*C11B 9/00* (2006.01)
*C11D 3/00* (2006.01)
*C11D 3/50* (2006.01)

(52) U.S. Cl.
CPC .......... *C11B 9/0003* (2013.01); *C07D 319/08* (2013.01); *C11B 9/0015* (2013.01); *C11D 3/001* (2013.01); *C11D 3/50* (2013.01)

(58) Field of Classification Search
None
See application file for complete search history.

(56) References Cited

U.S. PATENT DOCUMENTS

| | | | |
|---|---|---|---|
| 4,137,180 A | 1/1979 | Naik et al. | |
| 5,236,615 A | 8/1993 | Trinh et al. | |
| 5,739,100 A | 4/1998 | Horino et al. | |
| 2003/0083376 A1 | 5/2003 | Eh et al. | |

FOREIGN PATENT DOCUMENTS

| | | |
|---|---|---|
| DE | 19718537 A1 | 11/1998 |
| EP | 799885 A1 | 10/1997 |
| EP | 1262473 A1 | 12/2002 |
| EP | 1285906 A2 | 2/2003 |
| EP | 2287159 A1 | 2/2011 |
| IN | 2009DE00656 | 1/2011 |
| WO | WO1995016660 A1 | 6/1995 |
| WO | WO1997034986 A1 | 9/1997 |
| WO | WO1998006803 A1 | 2/1998 |
| WO | WO2000004009 A1 | 1/2000 |
| WO | WO2000038616 A2 | 7/2000 |
| WO | WO2003082850 A1 | 10/2003 |
| WO | WO2008011742 A1 | 1/2008 |

OTHER PUBLICATIONS

Yang, H. et al., J. Org. Chem. (2011), vol. 76, pp. 2040-2048.*
International Search Report and Written Opinion, application PCT/EP2016/050964 dated Mar. 8, 2016.
Ullmann's Encyclopedia of Industrial Chemistry, "Laundry Detergents, 1. Introduction", 2012, vol. 20, pp. 355-392.
Ullmann's Encyclopedia of Industrial Chemistry, "Laundry Detergents, 2. Ingredients and Products", 2012, vol. 20, pp. 393-450.
Ullmann's Encyclopedia of Industrial Chemistry, "Laundry Detergents, 3. Production, Testing and Economic Aspects", 2012, vol. 20, pp. 451-485.
Ullmann's Encyclopedia of Industrial Chemistry, "Laundry Detergents, 4. Ecology and Toxicology", 2012, vol. 20, pp. 487-520.
Ullmann's Encyclopedia of Industrial Chemistry, "Laundry Detergents, 5. Washing conditions and Washing Machines", 2012, vol. 20, pp. 521-540.
Wang et al., "Photolabile Carbonyl Protecting Group: A New Tool for Light-Controlled Release of Anticancer agents", 2009, Eur. J. Org. Chem., pp. 2055-2058.
Wang et al., "Sequential Removal of Photolabile Protecting Groups from Carbonyls with Controlled Wavelength", 2008, J. Org. Chem., vol. 73, pp. 6152-6157.
Wang et al., "Novel Photolabile Protecting Group for Carbonyl Compounds", Org. Lett., 2007, vol. 9(8), pp. 1533-1535.
Yang et al., "Development of a Photolabile Carbonyl-Protecting Group Toolbox", J. Org. Chem., 2011, vol. 76, pp. 2040-2048.

* cited by examiner

*Primary Examiner* — Heidi Reese
(74) *Attorney, Agent, or Firm* — Armstrong Teasdale LLP

(57) ABSTRACT

The present invention relates to a delivery system based on photosensitive acetal or ketal compounds capable of liberating upon exposure to light an active volatile carbonyl compound in a controlled manner from a surface into the surrounding. The delivery system can be used to release active substances such as flavors, fragrances, malodor counteractants, insect attractants or insect repellents. The invention also relates to the use of said acetal or ketal compounds in perfumery, as well as in perfuming compositions or perfumed consumer articles.

20 Claims, No Drawings

PHOTOLABILE ACETAL AND KETAL COMPOUNDS FOR THE CONTROLLED RELEASE OF ACTIVE VOLATILE CARBONYL COMPOUNDS

RELATED APPLICATIONS

This application is a national stage application under 35 U.S.C. § 371 filing of International Patent Application PCT/EP2016/050964, filed Jan. 19, 2016, which claims the benefit of European patent application n° 15151980.8 filed Jan. 21, 2015.

TECHNICAL FIELD

The present invention relates to the field of perfumery. More particularly, it concerns a delivery system based on photosensitive acetal or ketal compounds of formula (I) capable of liberating active volatile carbonyl compounds in a controlled manner upon exposure to light. The present invention also concerns the use of said acetal or ketal compounds in perfumery, as well as in perfuming compositions or perfumed consumer articles.

BACKGROUND

Flavors and fragrances, but also insect attractants or repellents, are volatile molecules that can only be perceived over a limited period of time.

The perfume industry has a particular interest for compositions or additives which are capable of prolonging or enhancing the perfuming effect of a mixture of several fragrances at the same time over a certain period of time. It is particularly desirable to obtain long-lasting properties for standard perfumery raw materials which are too volatile or have a poor substantivity by themselves, or which are only deposited in a small amount onto the surface of the final application. Furthermore, some of the perfumery ingredients, especially aldehydes, are unstable and need to be protected against slow degradation prior to their use. Long-lasting perfumes are desirable for various applications, as for example fine or functional perfumery or cosmetic preparations. The washing and softening of textiles is a particular field in which there is a constant quest to enable the effect of active substances, in particular perfumes, to be effective for a certain period of time after washing, softening and drying. Indeed, many substances having odors which are particularly suitable for this type of application are known to lack tenacity on laundry, or do not remain on the laundry when rinsed, with the result that their perfuming effect is experienced only briefly and not very intensely. Given the importance of this type of application in the perfume industry, research in this field has been sustained, in particular with the aim of finding new, and more effective solutions to the aforementioned problems.

A variety of precursor compounds which release active material by a chemical reaction during or after application (using $O_2$, light, enzymes, water (pH) or temperature as the release trigger) have been described as an alternative to encapsulation systems. In general, due to their inherent instability, the precursors often decompose in the application base during storage and thus release their fragrance raw material before the desired use.

In WO 95/16660, WO 97/34986, WO 98/06803 and EP 1 285 906, for example, acyclic acetals or related structures, which are capable of releasing mixtures of fragrance alcohols and aldehydes, have been reported. Said derivatives require hydrolytic conditions. From these systems, the fragrances are released as a pre-defined stoichiometric mixture of alcohols and aldehydes in a ratio of 2:1. This pre-defined mixture is not necessarily the ratio in which, for hedonic reasons, a person skilled in the art would like these compounds to be delivered. Furthermore, linear acetals and ketals are often quite unstable in a water-based environment, and therefore they are (at least in part) prematurely hydrolysed in water-containing consumer articles. On the other hand, cyclic acetals or ketals, as well as some related structures, such as those reported in DE 197 18 537, WO 00/04009, WO 00/38616, WO 2008/011742 or IN 2009DE00656 are often too stable to be efficiently used under mild application conditions because they typically require relatively harsh hydrolytic conditions and/or heating to be cleaved.

Stable acetals or ketals that could release fragrance aldehydes or ketones under mild reaction conditions by a trigger that is not based on hydrolysis would be advantageous for practical applications. In particular, the use of (natural) daylight as the trigger would be particularly suitable for the targeted use in perfumed consumer articles. The conjugates could easily be stored using opaque packing materials and, once deposited on the target surface and exposed to ambient daylight, slowly release the active compounds by light-induced covalent bond cleavage.

EP 1 262 473 reports 1-phenyl-2,2-bisalkoxy-ethanones as light sensitive precursors for the release of fragrance aldehydes and ketones. The light-induced cleavage of the precursor generates a pre-defined mixture of different fragrance compounds. Furthermore, the reaction mechanism involved in the cleavage of the conjugates gives rise to a series of different side-products which, from an application point of view might not be suitable.

Org. Lett., 2007, 9, 1533-1535, J. Org. Chem., 2008, 73, 6152-6157 and J. Org. Chem., 2011, 76, 2040-2048 describe a photolabile cleavage approach for carbonyl groups protected as acetals or ketals based on 5-methoxysalicilic alcohol. The photodeprotection is preferably conducted in the presence of water. In Eur. J. Org. Chem., 2009, 2055-2058, Wang and co-workers describe the light-controlled release of anticancer agents; however, these compounds are very hydrophilic and non-volatile. Furthermore, they are released into an aqueous environment and not meant to be deposited and evaporated from a surface to impart their benefits.

We have now surprisingly found that the photosensitive acetal and ketal compounds according to the present invention solve the above-mentioned problems and are capable of efficiently liberating active volatile carbonyl compounds upon exposure to light in numerous practical applications. To the best of our knowledge, none of the above documents suggests, or allows to expect, that the photosensitive acetal and ketal compounds of formula (I) could indeed be suitable as delivery systems for the controlled release of volatile compounds.

DESCRIPTION OF THE INVENTION

We have now surprisingly found that acetal or ketal compounds of formula

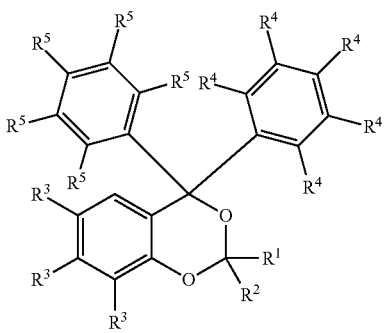

(I)

wherein $R^1$ and $R^2$, simultaneously or independently, represent a hydrogen atom, or a $C_{1-18}$ hydrocarbon group optionally comprising one to three oxygen atoms and/or one to two nitrogen atoms and/or one sulfur atom, provided than at least one of both is a $C_{1-18}$ hydrocarbon group; and derived from an active aldehyde (i.e. $R^2$ is a hydrogen atom) or ketone of formula $(R^1)(R^2)C(=O)$; said aldehyde or ketone having a molecular weight comprised between 80 and 230 g/mol and being a $C_{5-18}$ compound;

$R^3$ represent simultaneously or independently from each other, a hydrogen atom, a linear $C_1$-$C_8$ alkyl group, a branched or cyclic $C_3$-$C_8$ alkyl group, a hydroxy group, a methoxy group, an ethoxy group, a 2-hydroxyethoxy group, a 2-ethoxyethoxy group, a $(OCH_2CH_2)_nOH$ group, a $(OCH_2CH_2)_nOCH_3$ group, a methylthio group, a dimethylamino group, or a diethylamino group, with n being an integer varying between 2 and 8;

$R^4$ and $R^5$ represent, simultaneously or independently, from each other, a hydrogen atom, a linear $C_1$-$C_4$ alkyl group, a branched $C_3$-$C_4$ alkyl group, a methoxy group, an ethoxy group, a 2-hydroxyethoxy group, a 2-ethoxyethoxy group, a $(OCH_2CH_2)_nOH$ group, a $(OCH_2CH_2)_nOCH_3$ group, a methylthio group, a dimethylamino group, or a diethylamino group, with n having the same meaning as above;

can advantageously be used as a delivery system to release active volatile aldehydes or ketones from a given surface into the surrounding environment upon exposure to light.

By the terms "active compounds", "active volatile compounds", "active volatile aldehyde or ketone" or the similar, it is meant here that the aldehyde or ketone to which it is referred is capable of bringing a benefit or effect into its surrounding environment, and in particular the active compound is selected from the group consisting of a perfuming ingredient, flavoring ingredient, malodor counteracting ingredient and insect repellent or attractant ingredient. Therefore, for example, said "active aldehyde or ketone" possesses at least one property which renders it useful as perfuming or flavoring ingredient, as malodor counteracting ingredient and/or as insect repellent or attractant. For a person skilled in the art it is also evident that said active aldehydes or ketones are inherently volatile compounds.

By "insect attractant or repellent" it is meant a compound having a positive or negative effect on insects. Examples of such ingredients can be found in reference texts or in other works of a similar nature as for example: A. M. El-Sayed, The Pherobase 2005, http://www.pherobase.net.

According to all the above and below mentioned embodiments of the invention, the invention's delivery system is particularly useful when the active volatile aldehyde or ketone is a perfuming ingredient, i.e. a perfuming aldehyde or ketone. A "perfuming aldehyde or ketone" is a compound, which is of current use in the perfumery industry, i.e. a compound which is used as active ingredient in perfuming preparations or compositions in order to impart a hedonic effect. In other words, such an aldehyde or ketone, to be considered as being a perfuming one, must be recognized by a person skilled in the art of perfumery as being able to impart or modify in a positive or pleasant way the odor of a composition, and not just as having an odor. Said perfuming aldehydes or ketones can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery.

From now on we will refer to said "perfuming aldehyde or ketone" also as "perfuming compounds".

Practically, the invention is carried out exactly in the same manner, independently of the exact properties of the active aldehyde or ketone. Therefore, it is understood that, even if the invention will be further illustrated herein below with a specific reference to "perfuming compounds", the below embodiments are also applicable to other active aldehydes or ketones (i.e. it is possible to replace the expression "perfuming" with "flavoring", "malodor counteracting", "insect attractant" or with "insect repellent" for instance). According to a particular embodiment of the invention, active aldehydes are preferably used.

It is understood that by " . . . hydrocarbon group . . . " it is meant that said group consists of hydrogen and carbon atoms and can be in the form of an aliphatic hydrocarbon, i.e. linear or branched saturated hydrocarbon (e.g. alkyl group), a linear or branched unsaturated hydrocarbon (e.g. alkenyl or alkynil group), a saturated cyclic hydrocarbon (e.g. cycloalkyl) or an unsaturated cyclic hydrocarbon (e.g. cycloalkenyl or cycloalkynyl), or can be in the form of an aromatic hydrocarbon, i.e. aryl group, or can also be in the form of a mixture of said type of groups, e.g. a specific group may comprise a linear alkyl, a branched alkenyl (e.g. having one or more carbon-carbon double bonds), a (poly)cycloalkyl and an aryl moiety, unless a specific limitation to only one type is mentioned. Similarly, in all the embodiments of the invention, when a group is mentioned as being in the form of more than one type of topology (e.g. linear, cyclic or branched) and/or being saturated or unsaturated (e.g. alkyl, aromatic or alkenyl), it is also meant a group which may comprise moieties having any one of said topologies or being saturated or unsaturated, as explained above. Similarly, in all the embodiments of the invention, when a group is mentioned as being in the form of one type of saturation or unsaturation, (e.g. alkyl), it is meant that said group can be in any type of topology (e.g. linear, cyclic or branched) or having several moieties with various topologies.

For the sake of clarity, by the expression "containing one to three oxygen atoms and/or one to two nitrogen atoms and/or one sulfur atom", or the similar, in the present invention it is meant that the group, to which is made reference, may include functional groups such as for examples amines, thiols, thioethers, ethers, acetals, esters, nitriles, aldehydes, ketones, amides, carboxylates or alcohols.

According to any embodiment of the invention, $R^1$ and $R^2$ represent a hydrogen atom, or a $C_{1-15}$ hydrocarbon group optionally comprising one to two oxygen atoms and/or one nitrogen atom, provided than at least one of both is a $C_{1-15}$ hydrocarbon group; and derived from an active aldehyde (i.e. $R^2$ is an hydrogen atom) or ketone of formula $(R^1)(R^2)C(=O)$; said aldehyde or ketone having a molecular weight comprised between 80 and 230 g/mol and being a $C_{5-15}$ compound. In a preferred embodiment of the invention, $R^2$ represents a hydrogen atom and the corresponding active aldehyde is of formula $R^1CH(=O)$.

According to any embodiment of the invention, at least two $R^4$ and/or at least two $R^5$ are hydrogen atoms. More preferably, at least three $R^4$ and/or at least three $R^5$ are hydrogen atoms. Even more preferably, at least four $R^4$ and/or at least four $R^5$ are hydrogen atoms. Preferably the $R^4$ and $R^5$ groups in ortho position with respect to the bond between the aromatic ring and the oxygenated ring are hydrogen atoms, even more preferably the $R^4$ and $R^5$ groups in ortho and para position with respect to the bond between the aromatic ring and the oxygenated ring are hydrogen atoms.

According to any embodiment of the invention, all of the groups $R^4$ and $R^5$, which are not a hydrogen atom, represent the same group selected from the group consisting of a linear $C_1$-$C_4$ alkyl group, a branched $C_3$-$C_4$ alkyl group, a methoxy group, an ethoxy group, a $(OCH_2CH_2)_nOH$ group, a $(OCH_2CH_2)_nOCH_3$ group, a methylthio group, a dimethylamino group, and a diethylamino group with n having the same meaning as above. Preferably, all of the groups $R^4$ and $R^5$, which are not a hydrogen atom, represent the same group selected from the group consisting of a methoxy group, a methylthio group, a dimethylamino group, and a diethylamino group. Even more preferably, all of the groups $R^4$ and $R^5$, which are not a hydrogen atom, represent the same group selected from the group consisting of a methylthio group, a dimethylamino group, and a diethylamino group, even more preferably a methylthio group.

According to any embodiment of the invention, $R^4$ and $R^5$ are preferably a hydrogen atom, a methoxy group, a methylthio group, a dimethylamino group or a diethylamino group.

According to any embodiment of the invention, preferably at least one $R^4$ and/or one $R^5$ are a methoxy group, a methylthio group, a dimethylamino group or a diethylamino group; more preferably at least one $R^4$ and/or one $R^5$ are a methylthio group, a dimethylamino group or a diethylamino group, even more preferably, at least one $R^4$ and/or one $R^5$ are a methylthio group.

According to any embodiment of the invention, preferably one $R^4$ and one $R^5$ are a methoxy group, a methylthio group, a dimethylamino group or a diethylamino group and the four others $R^4$ and $R^5$ are hydrogen atom; more preferably one $R^4$ and one $R^5$ are a methylthio group, a dimethylamino group or a diethylamino group and the four others $R^4$ and $R^5$ are hydrogen atom; even more preferably, more preferably one $R^4$ and one $R^5$ are a methylthio group and the four others $R^4$ and $R^5$ are hydrogen atom. Preferably, the one $R^4$ and one $R^5$ being a methoxy group, a methylthio group, a dimethylamino group or a diethylamino group are in meta position with respect to the bond between the aromatic ring and the oxygenated ring.

According to any embodiment of the invention, $R^3$ represents preferably a hydrogen atom, a linear $C_1$-$C_4$ alkyl group, a branched $C_3$-$C_4$ alkyl group, a methoxy group, a dimethylamino group or a diethylamino group. Even more preferably, $R^3$ represents a hydrogen atom, a methyl group, a methoxy group, a dimethylamino group or a diethylamino group.

According to any embodiment of the invention, at least one $R^3$ represents a hydrogen atom. More preferably, at least two $R^3$ represents a hydrogen atom. Even more preferably, at least three $R^3$ represents a hydrogen atom.

According to any of the embodiments, the compound of formula (I) is advantageously characterized by a vapor pressure below 0.01 Pa, as obtained by calculation using the software EPIwin v. 3.10 (2000, available at the US Environmental Protection Agency). According to a preferred embodiment, said vapor pressure is below 0.001 Pa.

As mentioned above, the compound of the invention is capable, upon exposure to light, of releasing an active aldehyde or ketone (of formula $R^1CHO$ or $(R^1)(R^2)C(=O)$ respectively) having a specific molecular weight. According to a particular embodiment of the invention, said active aldehyde or ketone, comprises between 6 and 15 carbon atoms.

Furthermore, according to any of the embodiments, said active aldehyde or ketone is advantageously characterized by a vapor pressure above 1.0 Pa, as obtained by calculation using the software EPIwin v. 3.10 (2000, available at the US Environmental Protection Agency). According to another embodiment, said vapor pressure is above 5.0, or even above 7.0 Pa.

In an even more preferred embodiment, said active aldehydes of formula $R^1CHO$ are selected from the group consisting of 1,3-benzodioxol-5-carboxaldehyde (heliotropine), 3-(1,3-benzodioxol-5-yl)-2-methylpropanal, 2,4-decadienal, 2-decenal, 4-decenal, 8-decenal, 9-decenal, 3-(6,6-dimethyl-bicyclo[3.1.1]hept-2-en-2-yl)propanal, 2,4-dimethyl-3-cyclohexene-1-carbaldehyde (Triplal®, origin: International Flavors & Fragrances, New York, USA), 3,5-dimethyl-3-cyclohexene-1-carbaldehyde, 1-(3,3-dimethyl-1-cyclohexyl)-1-ethanone, 5,9-dimethyl-4,8-decadienal, 2,6-dimethyl-5-heptenal (melonal), 3,7-dimethyl-2,6-octadienal (citral), 3,7-dimethyloctanal, 3,7-dimethyl-6-octenal (citronellal), (3,7-dimethyl-6-octenyl)acetaldehyde, 3-dodecenal, 4-dodecenal, 3-ethoxy-4-hydroxybenzaldehyde (ethyl vanillin), 4-ethyl benzaldehyde, 3-(2 and 4-ethylphenyl)-2,2-dimethylpropanal, 2-furancarbaldehyde (furfural), 2,4-heptadienal, 4-heptenal, 2-hexenal, 3-hexenal, 2-hexyl-3-phenyl-2-propenal (hexylcinnamic aldehyde), 2-hydroxybenzaldehyde, 7-hydroxy-3,7-dimethyloctanal (hydroxycitronellal), 4-hydroxy-3-methoxybenzaldehyde (vanillin), 4- and 3-(4-hydroxy-4-methylpentyl)-3-cyclohexene-1-carbaldehyde (Lyral®, origin: International Flavors and Fragrances, New York, USA), 4-isopropylbenzaldehyde (cuminaldehyde), 3-(4-isopropylphenyl)-2-methylpropanal, 2-(4-isopropylphenyl)propanal, (4R)-1-p-menthene-9-carbaldehyde (Liminal®, origin: Firmenich SA, Geneva, Switzerland), 6-methoxy-2,6-dimethylheptanal (methoxymelonal), 8(9)-methoxy-tricyclo[5.2.1.0.(2,6)]decane-3(4)-carbaldehyde (Scentenal®, origin: Firmenich SA, Geneva, Switzerland), 4-methylbenzaldehyde (anisaldehyde), 2-(4-methylenecyclohexyl)propanal, 1-methyl-4-(4-methyl-3-pentenyl)-3-cyclohexen-1-carbaldehyde (Precyclemone® B, origin: International Flavors & Fragrances, New York, USA), 4-(4-methyl-3-pentenyl)-3-cyclohexene-1-carbaldehyde (Empetal, origin: Givaudan-Roure SA., Vernier, Switzerland), (4-methylphenoxy)acetaldehyde, (4-methylphenyl)acetaldehyde, 3-methyl-5-phenylpentanal (Phenexal®, origin: Firmenich SA, Geneva, Switzerland), 2-(1-methylpropyl)-1-cyclohexanone, 2,4-nonadienal, 2,6-nonadienal, 2-nonenal, 3-nonenal, 6-nonenal, 8-nonenal, 2-octenal, phenoxyacetaldehyde, phenylacetaldehyde, 3-phenylbutanal (Trifernal®, origin: Firmenich SA, Geneva, Switzerland), 2-phenylpropanal (hydratropaldehyde), 3-phenyl-2-propenal (cinnamic aldehyde), 3-(4-tert-butylphenyl)-2-methylpropanal (Lilial®, origin: Givaudan-Roure SA, Vernier, Switzerland), 3-(4-tert-butylphenyl)propanal (Bourgeonal®, origin: Quest International, Naarden, Netherlands), tricyclo[5.2.1.0(2,6)]decane-4-carbaldehyde, exo-tricyclo[5.2.1.0(2,6)]decane-8exo-carbaldehyde (Vertral®, origin: Symrise, Holzminden, Germany), 2,6,6-trimethyl-bicyclo[3.1.1]heptane-3-carbaldehyde (formyl pinane), 2,4,6- and 3,5,6-trimethyl-3-cyclohexene-1-carbaldehyde, 2,2,3-trimethyl-3-cyclopentene-1-acetaldehyde (campholenic aldehyde), 2,6,10-trimethyl-2,6,9,11-dodecatetraenal, 2,5,6-trimethyl-4-heptenal, 3,5,5-trimethylhexanal, 2,6,10-trimethyl-9-undecenal, 2-undecenal, 10-undecenal or 9-undecenal and their mixtures such as Intreleven aldehyde (origin: International Flavors & Fragrances, New York, USA) and Aldehyde Supra (origin: Firmenich SA, Geneva, Switzerland); wherein the underlined compounds represent, in an even more preferred embodiment of the invention, particularly useful fragrance aldehydes.

Respectively, said active ketone of formula $(R^1)(R^2)C(=O)$ is preferably selected from the group consisting of damascenones, damascones, ionones, methyl ionones (such as Iralia® Total, origin: Firmenich SA, Geneva, Switzerland), irones, cyclopentadecanone (Exaltone®, origin: Firmenich SA, Geneva, Switzerland), 3-methyl-4-cyclopentadecen-1-one (origin: Firmenich SA, Geneva, Switzerland), 3-methyl-5-cyclopentadecen-1-one (Delta Muscenone, origin: Firmenich SA, Geneva, Switzerland), 3-methyl-1-cyclopentadecanone (Muscone, origin: Firmenich SA, Geneva, Switzerland), 1-(2-aminophenyl)-1-ethanone, 1-(5,5-dimethyl-1-cyclohexen-1-yl)-4-penten-1-one (Neobutenone®, origin: Firmenich SA, Geneva, Switzerland), 1-(3,3-dimethyl-1-cyclohexyl)-1-ethanone, 2,5-dimethyl-2-octen-6-one, 4,7-dimethyl-6-octen-3-one, (3,7-dimethyl-6-octenyloxy)acetaldehyde, 1-(2,4-dimethylphenyl)-1-ethanone, 4-(1,1-dimethylpropyl)-1-cyclohexanone (Orivone®, origin: International Flavors & Fragrances, New York, USA), 2,4-di-tert-butyl-1-cyclohexanone, ethyl 4-oxopentanoate, 1-(4-ethylphenyl)-1-ethanone, 2-hexyl-1-cyclopentanone, 2-hydroxy-3-methyl-2-cyclopenten-1-one, 4-(4-hydroxy-1-phenyl)-2-butanone (raspberry ketone), 1-(2- and 4-hydroxyphenyl)-1-ethanone, 4-isopropyl-2-cyclohexen-1-one, 1-(4-isopropyl-1-phenyl)-1-ethanone, 1(6),8-p-menthadien-2-one (carvone), 4(8)-p-menthen-3-one, 1-(1-p-menthen-2-yl)-1-propanone, menthone, (1R,4R)-8-mercapto-3-p-menthanone, 1-(4-methoxyphenyl)-1-ethanone, 7-methyl-2H,4H-1,5-benzodioxepin-3-one (Calone®, origin: C.A.L. SA, Grasse, France), 5-methyl-3-heptanone, 6-methyl-5-hepten-2-one, methyl 3-oxo-2-pentyl-1-cyclopentaneacetate (Hedione®, origin: Firmenich SA, Geneva, Switzerland), 1-(4-methylphenyl)-1-ethanone (4-methylacetophenone), 5-methyl-exo-tricyclo[6.2.1.0(2,7)]undecan-4-one, 3-methyl-4-(1,2,2-trimethylpropyl)-4-penten-2-one, 2-naphthalenyl-1-ethanone, 1-(octahydro-2,3,8,8-tetramethyl-2-naphthalenyl)-1-ethanone (isomeric mixture, Iso E Super®, origin: International Flavors & Fragrances, New York, USA), 3,4,5,6,6-pentamethyl-3-hepten-2-one, 2-pentyl-1-cyclopentanone (Delphone, origin: Firmenich SA, Geneva, Switzerland), 4-phenyl-2-butanone (benzylacetone), 1-phenyl-1-ethanone (acetophenone), 2- and 4-tert-butyl-1-cyclohexanone, 1-(4-tert-butylphenyl)-1-ethanone), 2,4,4,7-tetramethyl-6-octen-3-one, 1,7,7-trimethyl-bicyclo[2.2.1]heptan-2-one (camphor), 2,6,6-trimethyl-1-cycloheptanone, 2,6,6-trimethyl-2-cyclohexene-1,4-dione, 4-(2,6,6-trimethyl-2-cyclohexen-1-yl)-2-butanone (dihydroionone), 1-(2,4,4-trimethyl-2-cyclohexen-1-yl)-2-buten-1-one, 1-(3,5,6-trimethyl-3-cyclohexen-1-yl)-1-ethanone and 2,2,5-trimethyl-5-pentyl-1-cyclopentanone; wherein the underlined compounds represent, in an even more preferred embodiment of the invention, particularly useful fragrance ketones.

The compounds of formula (I) used as light-sensitive delivery systems can be prepared from commercially available salicylic acid derivatives in a two-step sequence. In the first step the salicylic acid derivative is transformed into a diol of formula

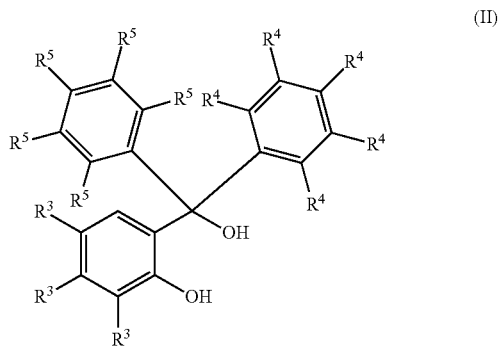

which is then further reacted with the active aldehyde of formula $R^1CHO$ or the active ketone of formula $(R^1)(R^2)C(=O)$ to be released to give the compound of formula (I) described above.

Owing to their particular chemical structure, the invention's delivery system of formula (I) is capable of releasing, via a decomposition reaction, a residue and an active ketone or aldehyde. The decomposition reaction, which leads to the release of the perfuming compounds, is believed to be triggered by light, in particular by light at a wavelength above 280 or even above 300 nm, or even above 330 nm.

In all aspects of the above-described invention the invention's delivery system might be used in the presence of other fragrance delivery systems, in particular in the presence of other light-sensitive fragrance delivery systems, or even in the presence of other delivery systems having a complementary release profile.

As mentioned above, the invention concerns the use of the above-described compounds of formula (I) as perfuming ingredients. In other words, it concerns a method to confer, enhance, improve or modify the odor properties of a perfuming composition or of a perfumed article, which method comprises adding to said composition or article an effective amount of at least a compound according to the invention. By "use of an invention's compound" it has to be understood here also the use of any composition containing said compounds and which can be advantageously employed in perfumery industry as active ingredients.

Said compositions, which in fact can be advantageously employed as perfuming ingredient, are also an object of the present invention.

Therefore, another object of the present invention is a perfuming composition comprising:
i) as perfuming ingredient, at least one of the invention's compounds as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid.

As liquid carriers one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as ethanol, water, dipropyleneglycol, diethyl phthalate, isopropyl myristate, benzyl benzoate, 2-(2-ethoxyethoxy)-1-ethanol or ethyl citrate, which are the most commonly used.

Generally speaking, by "perfumery base" we mean here a composition comprising at least one perfuming co-ingredient.

Said perfuming co-ingredient is not a compound according to the invention. Moreover, by "perfuming co-ingredient" it is meant here a compound, which is used in a perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, aldehydes, ketones, esters, ethers, acetates, nitriles, terpene hydrocarbons, nitrogenous or *sulphurous* heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability and etc. A detailed description of the nature and type of adjuvant commonly used in perfuming bases cannot be exhaustive, but it has to be mentioned that said ingredients are well known to a person skilled in the art.

An invention's composition consisting of at least one of the invention's compounds of formula (I) and at least one perfumery carrier represents a particular embodiment of the invention as well as a perfuming composition comprising at least one of the invention's compounds, at least one perfumery carrier, at least one perfumery base, and optionally at least one perfumery adjuvant.

It is useful to mention here that the possibility to have, in the compositions mentioned above, more than one of the invention's compounds or other precursors of similar type is important as it enables the perfumer to prepare accords, perfumes, possessing the odor tonality of various compounds of the invention, creating thus new tools for their work.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

Furthermore, the invention's compounds can also be advantageously used in all the fields of modern perfumery, i.e. fine or functional perfumery, to positively impart or modify the odor of a consumer product into which said compound (I) is added. Consequently, another object of the present invention is represented by a perfuming consumer product comprising, as perfuming ingredient, at least one compound of formula (I), as defined above.

The invention's compounds can be added as such or as part of an invention's perfuming composition.

For the sake of clarity, it has to be mentioned that, by "perfuming consumer product" it is meant a consumer product which is expected to deliver at least a pleasant perfuming effect to the surface to which it is applied (e.g. skin, hair, textile, or hard surface). In other words, a perfuming consumer product according to the invention is a perfumed consumer product which comprises the functional formulation, as well as optionally additional benefit agents, corresponding to the desired consumer product, e.g. a conditioner, a detergent or an air freshener, and an olfactively effective amount of at least one invention's compound. For the sake of clarity, said perfuming consumer product is a non-edible product.

The nature and type of the constituents of the perfuming consumer product do not warrant a more detailed description here, which in any case would not be exhaustive, the skilled person being able to select them on the basis of his general knowledge and according to the nature and the desired effect of said product.

Non-limiting examples of suitable perfuming consumer products can be a perfume, such as a fine perfume, a cologne or an after-shave lotion; a fabric care product, such as a liquid or solid detergent, a unidose detergent (like a powder tablet, a liquid unidose or a multichamber unidose detergent), a fabric softener, a fabric refresher, an ironing water, a paper, a bleach, a carpet cleaner or a curtain-care product; a body-care product, such as a hair care product (e.g. a shampoo, a conditioner, a coloring preparation, a color care product, a hair shaping product or a hair spray), a cosmetic preparation (e.g. a skin cream or lotion, a vanishing cream or a deodorant or antiperspirant) or a skin-care product (e.g. a perfumed soap, shower or bath mousse, oil or gel, or a hygiene product); an air care product, such as an air freshener or a "ready to use" powdered air freshener; a home care product, such as a wipe, a dish detergent, a leather care product or a hard-surface (e.g. a floor, bath, sanitary or window) detergent; or a car care product, such as a polish, a wax or a plastic cleaner.

Some of the above-mentioned consumer products may represent an aggressive medium for the invention's compound, so that it may be necessary to protect the latter from premature decomposition, for example by encapsulation.

Preferred perfuming compositions or perfumed articles are perfumes, textile or hard-surface detergents, fabric softeners, shampoos, hair conditioners or air fresheners.

Typical examples of fabric detergents or softener compositions into which the compounds of the invention can be incorporated are described in WO 97/34986 or in U.S. Pat. Nos. 4,137,180 and 5,236,615 or EP 799 885. Other typical detergent and softening compositions which can be used are described in works such as Ullmann's Encyclopedia of Industrial Chemistry, Vol. 20, Wiley-VCH, Weinheim, p. 355-540 (2012); Flick, Advanced Cleaning Product Formulations, Noye Publication, Park Ridge, N.J. (1989); Showell, in Surfactant Science Series, vol. 71: Powdered Detergents, Marcel Dekker, New York (1988); Proceedings of the World Conference on Detergents (4th, 1998, Montreux, Switzerland), AOCS print.

The proportions in which the compounds according to the invention can be incorporated into the various aforementioned articles or compositions vary within a wide range of values. These values are dependent upon the nature of the article or product to be perfumed and on the desired olfactory effect as well as the nature of the co-ingredients in a given composition when the compounds according to the invention are mixed with perfuming co-ingredients, solvents or additives commonly used in the art.

For example, typical concentrations are in the order of 0.001% to 10% by weight, or even more, of the compounds of the invention based on the weight of the composition into which they are incorporated. Concentrations lower than these, such as in the order of 0.001% to 5% by weight, can be used when these compounds are applied directly in the perfuming or flavoring of the various consumer products mentioned hereinabove.

Another object of the present invention relates to a method for the perfuming of a surface or to a method for intensifying or prolonging the diffusion effect of the characteristic fragrance of an odoriferous ingredient on a surface, characterized in that said surface is treated in the presence of an invention's compound. Suitable surfaces are, in particular, textiles, hard surfaces, hair and skin.

Another object of the present invention is an acetal or ketal compound of formula

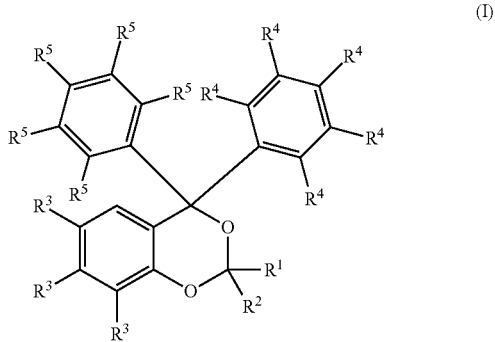

(I)

wherein $R^1$ and $R^2$, simultaneously or independently, represent a hydrogen atom, or a $C_{1-18}$ hydrocarbon group optionally comprising one to three oxygen atoms and/or one to two nitrogen atoms and/or one sulfur atom, provided than at least one of both is a $C_{1-18}$ hydrocarbon group; and derived from an active aldehyde (i.e. $R^2$ is a hydrogen atom) or ketone of formula $(R^1)(R^2)C(=O)$; said aldehyde or ketone having a molecular weight comprised between 80 and 230 g/mol and being a $C_{5-18}$ compound;

$R^3$ represent simultaneously or independently from each other, a hydrogen atom, a linear $C_1$-$C_8$ alkyl group, a branched or cyclic $C_3$-$C_8$ alkyl group, a hydroxy group, a methoxy group, an ethoxy group, a 2-hydroxyethoxy group, a 2-ethoxyethoxy group, a $(OCH_2CH_2)_nOH$ group, a $(OCH_2CH_2)_nOCH_3$ group, a methylthio group, a dimethylamino group, or a diethylamino group, with n being an integer varying between 2 and 8;

$R^4$ and $R^5$ represent, simultaneously or independently, from each other, a hydrogen atom, or a methylthio group, with at least one $R^4$ or $R^5$ being a methylthio group.

According to any embodiment of the invention the $R^4$ and $R^5$ groups in ortho position with respect to the bond between the aromatic ring and the oxygenated ring are hydrogen atoms, even more preferably the $R^4$ and $R^5$ groups in ortho and para position with respect to the bond between the aromatic ring and the oxygenated ring are hydrogen atoms.

EXAMPLES

The invention is hereafter described in more detailed manner by way of the following examples, wherein the abbreviations have the usual meaning in the art, temperatures are indicated in degrees centigrade (° C.). NMR spectral data were recorded on a Bruker 400, 500 or 600 MHz spectrometer in $CDCl_3$, if not specified otherwise, spectra were measured at 400 MHz for $^1H$ and at 100.6 MHz for $^{13}C$, the chemical displacements δ are indicated in ppm with respect to $Si(CH_3)_4$ as the standard, the coupling constants J are expressed in Hz (br.=broad peak). Commercially available reagents and solvents were used without further purification if not stated otherwise. Reactions were carried out in standard glassware under $N_2$.

The following examples illustrate delivery systems using perfuming or flavoring ingredients as active aldehydes or ketones. However, they are also representative for delivery systems according to the present invention in which the active aldehydes or ketones are useful as malodor counteractants, insect repellants or attractants. Some of the compounds described in the following examples, such as 2-heptanone or 10-undecenal, are also known to be insect attractants or repellents (see for example: A. M. El-Sayed, The Pherobase 2005, http://www.pherobase.net).

Example 1

Preparation of Non-Commercial Diols of Formula (II) According to the Invention a) Synthesis of 2-(bis(3-(dimethylamino)phenyl) (hydroxy)methyl)phenol Phenyllithium (2 M in cyclohexane, 9.86 mL, 19.7 mmol) was added during 15 min to a solution of methyl salicylate (3.00 g, 19.7 mmol) in tetrahydrofuran (THF, 20 mL) at −78° C. After stirring for 5 min at −78° C., the reaction mixture was transferred during 20 min to a Grignard reagent prepared from 3-bromo-N,N-dimethylaniline (7.89 g, 39.4 mmol) and magnesium turnings (1.15 g, 47.3 mmol) in THF (ca. 110 mL), which was maintained at 0° C. during the addition. The reaction mixture was left warming to room temperature. After stirring at room temperature for 24 h, the reaction mixture was decanted and quenched with a saturated solution of ammonium chloride (ca. 200 mL). Extraction with ethyl acetate, drying ($Na_2SO_4$) and concentrating gave 7.97 g of the crude product. Column chromatography ($SiO_2$, heptane/ethyl acetate 3:1) finally yielded 2.15 g (30%) of the target compound.

$^1$H-NMR: 7.20-7.12 (m, 3H), 6.88-6.84 (m, 1H), 6.74-6.70 (m, 1H), 6.70-6.65 (m, 4H), 6.64-6.60 (m, 1H), 6.53-6.48 (m, 2H), 3.70 (br. s, 1H), 2.84 (s, 12H).

¹³C-NMR: 156.25, 150.35, 145.92, 130.37, 130.18, 129.23, 128.60, 118.77, 117.30, 116.58, 112.36, 112.01, 85.01, 40.59.

b) Synthesis of 2-(bis(3-(dimethylamino)phenyl)(hydroxy)methyl)-6-methoxyphenol

As described above with phenyllithium (2 M in cyclohexane, 15.04 mL, 30.1 mmol), methyl 3-methoxysalicylate (5.00 g, 27.4 mmol) in THF (35 mL), 3-bromo-N,N-dimethylaniline (12.04 g, 60.2 mmol), magnesium turnings (1.76 g, 72.2 mmol) in THF (ca. 320 mL) and ammonium chloride (ca. 150 mL). Column chromatography (SiO$_2$, heptane/ethyl acetate 3:1, then pure ethyl acetate) finally yielded 3.33 g (31%) of the target compound.

¹H-NMR: 7.12 (t, 2H), 6.87-6.84 (m, 2H), 6.83-6.78 (m, 1H), 6.71-6.63 (m, 3H), 6.53-6.47 (m, 2H), 6.24 (dd, 1H), 4.84 (br. s, 1H), 3.85 (s, 3H), 2.86 (s, 12H).

¹³C-NMR: 150.28, 146.95, 146.89, 143.67, 132.97, 128.09, 122.63, 118.70, 116.89, 112.44, 111.60, 110.24, 82.93, 56.13, 40.68.

c) Synthesis of 2-(bis(3-(dimethylamino)phenyl)(hydroxy)methyl)-4-methoxyphenol

As described above with phenyllithium (1.9 M in dibutylether, 10.37 mL, 19.7 mmol), methyl 2-hydroxy-5-methoxybenzoate (3.60 g, 19.7 mmol) in THF (20 mL), 3-bromo-N,N-dimethylaniline (7.88 g, 39.4 mmol) and magnesium turnings (1.15 g, 47.3 mmol) in THF (ca. 60 mL). Flash chromatography (SiO$_2$, heptane/ethyl acetate 3:1) yielded 4.1 g (53%) of the target compound.

¹H-NMR (500 MHz): 7.80 (br. s, 1H), 7.15 (t, J=7.9, 2H), 6.80 (d, J=9.3, 1H), 6.74 (dd, J=8.8, 3.0, 1H), 6.71-6.54 (m, 4H), 6.53-6.48 (m, 2H), 6.24 (d, J=3.0, 1H), 3.70 (br. s, 1H), 3.61 (s, 3H), 2.85 (s, 12H).

¹³C-NMR (125.8 MHz): 152.02, 150.39, 150.14, 145.74, 131.42, 128.61, 117.61, 116.71, 116.55, 113.69, 112.25, 112.06, 84.73, 55.71, 40.61.

d) Synthesis of 2-(bis(3-(dimethylamino)phenyl)(hydroxy)methyl)-6-methylphenol

As described above with phenyllithium (2 M in cyclohexane, 15.04 mL, 30.1 mmol), methyl 2-hydroxy-3-methylbenzoate (5.00 g, 30.1 mmol) in THF (35 mL), 3-bromo-N,N-dimethylaniline (12.04 g, 60.2 mmol), magnesium turnings (1.76 g, 72.2 mmol) in THF (ca. 320 mL) and ammonium chloride (ca. 150 mL). Flash chromatography (SiO$_2$, heptane/ethyl acetate 3:1, then pure ethyl acetate) yielded 5.6 g (49%) of the target compound.

¹H-NMR: 8.40 (s, 1H), 7.19-7.12 (m, 2H), 7.08-7.03 (m, 1H), 6.70-6.64 (m, 4H), 6.61 (t, J=7.6, 1H), 6.53-6.44 (m, 3H), 3.55 (s, 1H), 2.85 (s, 12H), 2.22 (s, 3H).

¹³C-NMR: 154.49, 150.32, 146.03, 130.49, 129.69, 128.57, 128.01, 125.92, 118.06, 116.54, 112.30, 111.95, 85.11, 40.58, 16.07.

e) Synthesis of 2-(hydroxybis(3-methoxyphenyl)methyl)-4-methoxyphenol

As described above with phenyllithium (2 M in cyclohexane, 13.72 mL, 27.4 mmol), methyl 2-hydroxy-5-methoxybenzoate (5.00 g, 27.4 mmol) in THF (35 mL), 3-bromo-N,N-dimethylaniline (10.27 g, 54.9 mmol), magnesium turnings (1.6 g, 65.9 mmol) in THF (ca. 170 mL) and ammonium chloride (ca. 200 mL) to give 13.09 g of a brown oil. Flash chromatography (SiO$_2$, heptane/ethyl acetate 3:1) finally yielded 2.67 g (27%) of the target compound.

¹H-NMR: 7.52 (s, 1H), 7.22 (t, J=7.8, 2H), 6.86-6.80 (m, 4H), 6.80-6.71 (m, 4H), 6.15 (d, J=2.8, 1H), 4.01 (s, 1H), 3.72 (s, 6H), 3.60 (s, 3H).

¹³C-NMR: 159.41, 152.22, 149.62, 146.35, 131.18, 129.11, 120.28, 117.81, 116.59, 113.90, 113.74, 113.02, 83.83, 55.62, 55.20.

f) Synthesis of 2-(hydroxybis(3-(methylthio)phenyl)methyl)-4-methoxyphenol

As described above with phenyllithium (1.9 M in dibutylether, 10.40 mL, 19.8 mmol), methyl 2-hydroxy-5-methoxybenzoate (3.60 g, 19.7 mmol) in THF (20 mL), (3-bromophenyl)(methyl)sulfane (8.00 g, 39.4 mmol) and magnesium turnings (1.15 g, 47.3 mmol) in THF (ca. 50 mL) for 15 h. Quenching with a solution of ammonium chloride (10%) and flash chromatography (SiO$_2$, heptane/ethyl acetate 4:1) yielded 3.05 g (39%) of the target compound, still containing some solvent.

¹H-NMR (500 MHz): 7.42 (s, 1H), 7.26-7.14 (m, 6H), 6.95-6.87 (m, 2H), 6.80-6.71 (m, 2H), 6.13-6.09 (m, 1H), 4.19 (s, 1H), 3.60 (s, 3H), 2.38 (s, 6H).

¹³C-NMR (125.8 MHz): 152.30, 149.37, 145.34, 138.67, 131.01, 128.51, 125.83, 125.60, 124.66, 117.85, 116.59, 113.79, 83.64, 55.64, 15.64.

Example 2

Preparation of Photosensitive Acetal or Ketal Compounds of Formula (I) According to the Invention a) Synthesis of (+)-3,3'-(2-(9-decenyl)-4H-benzo[d][1,3]dioxine-4,4-diyl)bis(N,N-dimethylaniline)

A mixture of 2-(bis(3-(dimethylamino)phenyl)(hydroxy)methyl)phenol (0.50 g, 1.4 mmol) and 10-undecenal (0.46 g, 2.8 mmol) was stirred at 140° C. for 2 h to give the crude reaction product. Column chromatography (SiO$_2$, heptane/ethyl acetate 3:1) and bulb-to-bulb distillation (110° C., 0.2 mbar) to remove remaining 10-undecenal gave 0.61 g (86%) of the target compound.

¹H-NMR: 7.17 (t, 1H), 7.14-7.09 (m, 1H), 7.08 (t, 1H), 6.91-6.84 (m, 2H), 6.81-6.74 (m, 3H), 6.72-6.66 (m, 2H), 6.64-6.57 (m, 1H), 6.56-6.51 (m, 1H), 5.86-5.75 (m, 1H), 5.10-5.05 (m, 1H), 5.02-4.89 (m, 2H), 2.87 (s, 6H), 2.83 (s, 6H), 2.08-1.99 (m, 2H), 1.92-1.77 (m, 2H), 1.58-1.41 (m, 2H), 1.41-1.15 (m, 10H).

¹³C-NMR: 152.38, 150.31, 150.14, 147.02, 145.17, 139.21, 129.83, 128.29, 128.15, 127.94, 126.21, 119.75, 118.25, 117.41, 116.69, 114.11, 113.52, 112.93, 112.03, 111.67, 95.32, 84.68, 40.63, 40.61, 34.68, 33.80, 29.51, 29.45, 29.38, 29.12, 28.92, 23.57.

b) Synthesis of (+)-3,3'-(2-(6-methoxy-6-methylheptan-2-yl)-4H-benzo[d][1,3]dioxine-4,4-diyl)bis(N,N-dimethylaniline)

As described above in Example 2a with 2-(bis(3-(dimethylamino)phenyl)(hydroxy)methyl)phenol (1.00 g, 2.8 mmol) and (+)-6-methoxy-2,6-dimethylheptanal (methoxymelonal, 0.95 g, 5.5 mmol) to give the crude product. Bulb-to-bulb distillation (2×, 110° C., 2.0 mbar and 140° C., 0.2 mbar) to remove remaining (±)-6-methoxy-2, 6-dimethylheptanal gave 0.95 g (67%) of the target compound as a mixture of diastereoisomers.

$^1$H-NMR: 7.20-7.05 (m, 3H), 6.92-6.71 (m, 5H), 6.71-6.63 (m, 2H), 6.63-6.57 (m, 1H), 6.56-6.51 (m, 1H), 4.93 and 4.90 (d, 1H), 3.15 and 3.13 (s, 3H), 2.86 and 2.85 (s, 6H), 2.84 and 2.84 (s, 6H), 1.98-1.85 (m, 1H), 1.81-0.98 (m, 6H), 1.11 and 1.11 (s, 3H), 1.11 and 1.04 (d, 3H), 1.08 and 1.07 (s, 3H).

$^{13}$C-NMR: 152.50, 152.43, 150.28, 150.22, 150.08, 147.29, 147.24, 145.20, 145.13, 129.68, 128.25, 128.21, 128.11, 127.91, 126.03, 125.97, 119.60, 119.58, 118.38, 118.34, 117.31, 116.76, 113.73, 113.63, 112.84, 112.78, 112.05, 111.57, 111.53, 97.61, 97.08, 84.37, 84.27, 74.62, 74.58, 49.04, 49.02, 40.62, 40.60, 40.57, 39.90, 39.86, 37.60, 37.50, 31.85, 30.94, 25.01, 24.99, 24.87, 21.45, 21.39, 13.95, 13.33.

c) Synthesis of (+)-3,3'-(2-(2-phenylpropyl)-4H-benzo[d][1,3]dioxine-4,4-diyl)bis(N,N-dimethylaniline)

As described above in Example 2a with 2-(bis(3-(dimethylamino)phenyl)(hydroxy)methyl)phenol (1.00 g, 2.8 mmol) and (+)-3-phenylbutanal (Trifernal®, 0.82 g, 5.5 mmol) to give the crude product. Bulb-to-bulb distillation (130° C., 0.2 mbar) to remove remaining Trifernal® gave 1.45 g (quant.) of the target compound as a mixture of diastereoisomers.

$^1$H-NMR: 7.33-7.01 (m, 8H), 6.92-6.50 (m, 9H), 5.12-5.07 and 4.92-4.87 (m, 1H), 3.17-2.88 (m, 1H), 2.87 and 2.85 (s, 6H), 2.85 and 2.84 (s, 6H), 2.27-2.03 (m, 2H), 1.26 and 1.10 (d, 3H).

$^{13}$C-NMR: 152.39, 152.36, 150.27, 150.13, 147.29, 147.09, 146.83, 146.64, 145.07, 145.05, 129.75, 129.70, 128.53, 128.27, 128.31, 128.18, 128.18, 127.96, 127.83, 126.94, 126.76, 126.24, 126.09, 125.87, 125.76, 119.98, 119.86, 118.71, 118.36, 117.42, 116.77, 116.71, 114.39, 113.62, 112.93, 112.88, 112.25, 112.16, 111.70, 94.20, 84.90, 84.82, 43.43, 42.56, 40.72, 40.66, 34.96, 34.62, 22.73, 21.94.

d) Synthesis of (+)-3,3'-(2-(2,4,4-trimethylpentyl)-4H-benzo[d][1,3]dioxine-4,4-diyl)bis(N,N-dimethylaniline)

As described above in Example 2a with 2-(bis(3-(dimethylamino)phenyl)(hydroxy)methyl)phenol (1.00 g, 2.8 mmol) and (+)-3,5,5-trimethylhexanal (0.79 g, 5.5 mmol) to give the crude product. Bulb-to-bulb distillation (120° C., 0.6 mbar) to remove remaining (+)-3,5,5-trimethylhexanal gave 1.33 g (99%) of the target compound as a mixture of diastereoisomers.

$^1$H-NMR: 7.20-7.05 (m, 3H), 6.96-6.72 (m, 5H), 6.71-6.63 (m, 2H), 6.63-6.56 (m, 1H), 6.56-6.50 (m, 1H), 5.14-5.07 (m, 1H), 2.85 and 2.85 (s, 6H), 2.84 and 2.83 (s, 6H), 2.02-1.76 (m, 2H), 1.74-1.58 (m, 1H), 1.32-0.98 (m, 2H), 0.92 and 0.74 (d, 3H), 0.87 and 0.83 (s, 9H).

$^{13}$C-NMR: 152.38, 150.33, 150.31, 150.14, 147.03, 146.92, 145.40, 145.14, 129.74, 129.64, 128.31, 128.20, 128.11, 128.05, 127.94, 127.88, 126.17, 126.05, 119.76, 118.45, 118.34, 117.42, 116.77, 116.69, 113.80, 113.65, 112.86, 112.56, 112.25, 112.13, 111.63, 111.49, 94.73, 94.37, 84.74, 84.58, 51.56, 51.52, 44.26, 44.06, 40.63, 40.59, 31.24, 31.06, 30.08, 29.93, 25.15, 24.71, 23.04, 22.77.

e) Synthesis of 3,3'-(2-(9-decenyl)-8-methoxy-4H-benzo[d][1,3]dioxine-4,4-diyl)bis(N,N-dimethylaniline)

A mixture of 2-(bis(3-(dimethylamino)phenyl)(hydroxy)methyl)-6-methoxyphenol (1.03 g, 2.6 mmol), 10-undecenal (0.30 g, 1.8 mmol) and 4-methylbenzenesulfonic acid hydrate (0.03 g, 0.2 mmol) in toluene (11 mL) was heated under reflux with azeotropic removal of water for 3 h. The reaction mixture was left cooling to room temperature and concentrated. Flash chromatography (SiO$_2$, heptane/ethyl acetate 7:3, then pure ethyl acetate) and bulb-to-bulb distillation to remove remaining 10-undecenal gave 0.43 g (45%) of the target compound.

$^1$H-NMR: 7.16 (t, 1H), 7.07 (t, 1H), 6.81-6.76 (m, 2H), 6.75-6.66 (m, 4H), 6.61-6.57 (m, 1H), 6.55-6.48 (m, 2H), 5.87-5.73 (m, 1H), 5.08 (dd, 1H), 5.02-4.89 (m, 2H), 3.88 (s, 3H), 2.86 (s, 6H), 2.83 (s, 6H), 2.07-1.98 (m, 2H), 1.98-1.86 (m, 2H), 1.61-1.47 (m, 1H), 1.47-1.13 (m, 11H).

$^{13}$C-NMR: 150.27, 150.13, 147.96, 146.99, 145.11, 142.27, 139.23, 128.22, 128.09, 126.90, 121.87, 119.02, 118.37, 117.45, 114.09, 113.66, 112.90, 112.08, 111.67, 109.48, 95.72, 84.65, 55.92, 40.64, 40.61, 34.63, 33.80, 29.49, 29.38, 29.12, 28.93, 23.77.

f) Synthesis of 3,3'-(2-(dec-9-en-1-yl)-6-methoxy-4H-benzo[d][1,3]dioxine-4,4-diyl)bis(N,N-dimethylaniline)

As described above in Example 2e with 2-(bis(3-(dimethylamino)phenyl)(hydroxy)methyl)-4-methoxyphenol (0.92 g, 2.3 mmol), 10-undecenal (0.28 g, 1.7 mmol) and 4-methylbenzenesulfonic acid hydrate (0.04 g, 0.2 mmol) for 0.5 h. Repetitive flash chromatography (SiO$_2$, heptane/ethyl acetate 3:1 and 9:1) gave 0.24 g (26%) of the target compound.

$^1$H-NMR (500 MHz): 7.17 (t, J=7.9, 1H); 7.08 (t, J=8.0, 1H), 6.82-6.77 (m, 3H), 6.74-6.67 (m, 3H), 6.62-6.57 (m, 1H), 6.55-6.50 (m, 1H), 6.46 (d, J=3.0, 1H), 5.86-5.75 (m, 1H), 5.03-4.89 (m 3H), 3.62 (s, 3H), 2.87 (s, 6H), 2.84 (s, 6H), 2.06-1.99 (m, 2H), 1.90-1.75 (m, 2H), 1.58-1.39 (m, 2H), 1.39-1.16 (m, 10H).

$^{13}$C-NMR (125.8 MHz): 152.60, 150.32, 150.22, 146.89, 146.59, 145.16, 139.23, 128.23, 128.20, 126.66, 118.25, 117.32, 117.20, 114.97, 114.10, 113.96, 113.43, 112.80, 112.09, 111.74, 95.25, 84.69, 55.63, 40.67, 40.63, 34.66, 33.80, 29.51, 29.45, 29.39, 29.12, 28.93, 23.62.

g) Synthesis of 3,3'-(2-(dec-9-en-1-yl)-8-methyl-4H-benzo[d][1,3]dioxine-4,4-diyl)bis(N,N-dimethylaniline)

A mixture of 2-(bis(3-(dimethylamino)phenyl)(hydroxy)methyl)-6-methylphenol (1.00 g, 2.7 mmol), 10-undecenal (0.45 g, 2.7 mmol) and 4-methylbenzenesulfonic acid hydrate (0.57 g, 3.0 mmol) in toluene (20 mL) was heated under reflux with azeotropic removal of water for 2 h. The reaction mixture was left cooling to room temperature and the liquid phase concentrated. Repetitive flash chromatography (SiO$_2$, heptane/ethyl acetate 4:1 and 9:1) gave 0.14 g (10%) of the target compound, still containing some 10-undecenal.

$^1$H-NMR (600 MHz): 7.17 (t, J=7.9, 1H), 7.08 (t, J=8.1, 1H), 7.00-6.96 (m, 1H), 6.80-6.65 (m, 6H), 6.61-6.57 (m, 1H), 6.56-6.53 (m, 1H), 5.85-5.76 (m, 1H), 5.06 (t, J=5.0, 1H), 5.02-4.96 (m, 1H), 4.95-4.90 (m, 1H), 2.87 (s, 6H), 2.83 (m, 6H), 2.21 (s, 3H), 2.07-2.00 (m, 2H), 1.90-1.82 (m, 2H), 1.57-1.41 (m, 2H), 1.41-1.13 (m, 10H).

$^{13}$C-NMR (151.0 MHz): 150.56, 150.31, 150.11, 147.23, 145.48, 139.24, 128.94, 128.23, 128.12, 127.42, 125.65, 125.48, 118.90, 118.33, 117.47, 114.10, 113.57, 113.05, 111.97, 111.59, 95.25, 84.69, 40.68, 40.66, 34.72, 33.81, 29.54, 29.48, 29.41, 29.13, 28.93, 23.69, 15.76.

h) Synthesis of 2-(dec-9-en-1-yl)-6-methoxy-4,4-bis (3-methoxyphenyl)-4H-benzo[d][1,3]dioxine A mixture of 2-(hydroxybis(3-methoxyphenyl)methyl)-4-methoxyphenol (1.12 g, 3.1 mmol), 10-undecenal (0.37 g, 2.2 mmol) and 4-methylbenzenesulfonic acid hydrate (0.04 g, 0.2 mmol) in toluene (20 mL) was stirred at room temperature for 72 h. The reaction mixture was concentrated. Flash chromatography (SiO$_2$, heptane/ethyl acetate 3:1) gave 1.18 g (quant.) of the target compound.

$^{1}$H-NMR (500 MHz): 7.24 (t, J=7.9, 1H), 7.15 (t, J=8.0, 1H), 6.97-6.91 (m, 2H), 6.91-6.84 (m, 2H), 6.82 (d, J=9.0, 1H), 6.80-6.74 (m, 2H), 6.73 (dd, J=9.0, 3.2, 1 H), 6.40 (d, J=2.9, 1H), 5.85-5.75 (m, 1H), 5.02-4.89 (m, 3H), 3.74 (s, 3H), 3.72 (s, 3H), 3.63 (s, 3H), 2.06-1.99 (m, 2H), 1.91-1.75 (m, 2H), 1.54-1.31 (m, 4H), 1.31-1.10 (m, 8H).

$^{13}$C-NMR (125.8 MHz): 159.37, 159.19, 152.78, 147.48, 146.53, 145.83, 139.21, 128.87, 128.72, 125.76, 121.79, 120.76, 117.50, 114.91, 114.82, 114.26, 114.12, 114.10, 113.38, 112.51, 95.23, 83.99, 55.59, 55.20, 55.14, 34.51, 33.79, 29.47, 29.37, 29.35, 29.10, 28.91, 23.55.

i) Synthesis of 2-(dec-9-en-1-yl)-6-methoxy-4,4-bis (3-(methylthio)phenyl)-4H-benzo[d][1,3]dioxine A mixture of 2-(hydroxybis(3-(methylthio)phenyl) methyl)-4-methoxyphenol (1.0 g, 2.5 mmol), 10-undecenal (0.42 g, 2.5 mmol) and 4-methylbenzenesulfonic acid hydrate (0.05 g, 0.3 mmol) in cyclohexane (20 mL) was stirred under reflux with azeotropic removal of water for 2 h. The reaction mixture was left cooling to room temperature, washed with a saturated aqueous solution of NaHCO$_3$ (50 mL), dried (Na$_2$SO$_4$) and concentrated. Flash chromatography (SiO$_2$, heptane/ethyl acetate 9:1) gave 0.87 g (63%) of the target compound.

$^{1}$H-NMR (500 MHz): 7.29-7.08 (m, 7H), 6.95-6.90 (m, 1H), 6.83 (d, J=9.0, 1H), 6.75 (dd, J=9.0, 2.9, 1H), 6.36 (d, J=6.9, 1H), 5.85-5.75 (m, 1H), 5.02-4.88 (m, 3H), 3.64 (s, 3H), 2.41 (s, 3H), 2.39 (s, 3H), 2.06-1.99 (m, 2H), 1.89-1.74 (m, 2H), 1.52-1.31 (m, 4H), 1.31-1.17 (m, 8H).

$^{13}$C-NMR (125.8 MHz): 152.86, 146.56, 146.49, 144.82, 139.21, 138.60, 138.16, 128.40, 128.26, 126.84, 126.14, 125.99, 125.88, 125.56, 125.28, 125.12, 117.67, 114.90, 114.23, 114.11, 95.21, 83.84, 55.63, 34.45, 33.80, 29.47, 29.37, 29.34, 29.10, 28.91, 23.52, 15.77, 15.63.

Example 3

Preparation of Photosensitive Acetal or Ketal Compounds of Formula (I) with all R$^4$ and R$^5$ being Hydrogen Atoms a) Synthesis of 2-(hydroxydiphenylmethyl)phenol Bromobenzene (27.70 g, 176 mmol) was weighed into a dropping funnel, and about 50 drops of the pure compound were added to a suspension of magnesium turnings (5.10 g, 210 mmol) in ether (10 mL) and some crystals of iodine. Then ether (50 mL) was added to the remaining bromobenzene, and the solution added dropwise during 30 min. The reaction mixture was heated under reflux for 1 h. After cooling to room temperature, salicylic acid (2.89 g, 21 mmol) in ether (50 mL) was added dropwise during 30 min. The reaction mixture was left stirring at room temperature overnight, and then poured onto an aqueous solution of HCl (10%, 100 mL) and ice (100 g). Extraction with ether (2×100 mL), washing with an aqueous solution of NaOH (10%, 100 mL) and ice (50 mL), with a saturated aqueous solution of NaHCO$_3$ (2×50 mL), with a saturated aqueous solution of NaCl (2×50 mL), drying (Na$_2$SO$_4$) and concentrating afforded the crude product. The solid was taken up in ethyl acetate (2 mL) and heptane (5 mL) and left crystallizing in the fridge for 3 h. Filtration, concentrating, re-dissolving and re-crystallizing the mother liquor gave, after drying in a desiccator for 2 h, a total of 1.58 g (27%) of the target compound.

$^{1}$H-NMR (500 MHz): 8.13 (s, 1H), 7.36-7.29 (m, 6H), 7.23-7.16 (m, 5H), 6.86 (dd, J=8.1, 1.2, 1H), 6.73 (dt, J=7.5, 1.2, 1H), 6.51 (dd, J=7.9, 1.6, 1H), 3.77 (s, 1H).

$^{13}$C-NMR (125.8 MHz): 155.95, 144.84, 130.04, 129.99, 129.56, 128.17, 127.92, 127.76, 119.10, 117.56, 84.40.

Synthesis of (+)-2-(dec-9-en-1-yl)-4,4-diphenyl-4H-benzo[d][1,3]dioxine

A mixture of 2-(hydroxydiphenylmethyl)phenol (0.50 g, 1.8 mmol), 10-undecenal (0.20 g, 1.2 mmol) and 4-methylbenzenesulfonic acid hydrate (0.02 g, 0.1 mmol) in toluene (10 mL) was stirred at room temperature for 18 h. The reaction mixture was concentrated. Flash chromatography (SiO$_2$, heptane/ethyl acetate 7:1) gave 0.52 g (quant.) of the target compound.

$^{1}$H-NMR (500 MHz): 7.37-7.31 (m, 5H), 7.27-7.19 (m, 5H), 7.18-7.12 (m, 1H), 6.92-6.88 (m, 1H), 6.84-6.79 (m, 2H), 5.86-5.75 (m, 1H), 5.02-4.95 (m, 2H), 4.95-4.89 (m, 1H), 2.07-1.99 (m, 2H), 1.91-1.77 (m, 2H), 1.52-1.31 (m, 4H), 1.31-1.15 (m, 8H).

$^{13}$C-NMR (125.8 MHz): 152.49 (s), 146.22 (s), 144.32 (s), 139.22 (d), 129.83 (d), 129.27 (d), 128.27 (d), 128.19 (d), 128.00 (d), 127.92 (d), 127.79 (d), 127.42 (d), 125.44 (s), 120.03 (d), 117.02 (d), 114.11 (t), 95.23 (d), 84.11 (s), 34.48 (t), 33.79 (t), 29.44 (t), 29.36 (t), 29.30 (t), 29.09 (t), 28.90 (t), 23.40 (t).

b) Synthesis of 2-(hydroxydiphenylmethyl)-6-methoxyphenol

A solution of bromobenzene (30.40 g, 193 mmol) in ether (140 mL) was added dropwise during 1.2 h to a suspension of magnesium turnings (8.67 g, 357 mmol) in ether (20 mL). The reaction mixture was heated under reflux for 2 h. After cooling to room temperature, 3-methoxysalicylic acid (6.00 g, 35.7 mmol) in ether (140 mL) was added dropwise during 60 min, and the reaction mixture was left stirring at room temperature overnight. The reaction mixture was treated as described above to give 2.42 g (22%) of the target compound.

$^{1}$H-NMR: 7.34-7.22 (m, 10H), 6.85 (d, J=8.2, 1H), 6.70 (t, J=8.0, 1H), 6.36 (s, 1H), 6.13 (d, J=8.0, 1H), 5.00 (s, 1H), 3.88 (s, 3H).

$^{13}$C-NMR: 146.94, 146.06, 143.35, 132.56, 127.83, 127.78, 127.23, 122.33, 119.00, 110.34, 82.18, 56.17.

Synthesis of 2-(9-decenyl)-8-methoxy-4,4-diphenyl-4H-benzo[d][1,3]dioxine

A mixture of 2-(hydroxydiphenylmethyl)-6-methoxyphenol (1.00 g, 3.3 mmol), 10-undecenal (0.37 g, 2.2 mmol) and 4-methylbenzenesulfonic acid hydrate (0.04 g, 0.2 mmol) in toluene (11 mL) was stirred at room temperature for 72 h. The reaction mixture was concentrated. Flash chromatography (SiO$_2$, heptane/ethyl acetate 7:1, then ethyl acetate) gave 0.97 g (97%) of the target compound.

$^1$H-NMR: 7.39-7.30 (m, 5H), 7.28-7.18 (m, 5H), 6.79-6.72 (m, 2H), 6.46-6.39 (m, 1H), 5.86-5.74 (m, 1H), 5.03-4.89 (m, 3H), 3.89 (s, 3H), 2.06-1.98 (m, 2H), 1.98-1.85 (m, 2H), 1.53-1.41 (m, 1H), 1.41-1.30 (m, 3H), 1.30-1.12 (m, 8H).

$^{13}$C-NMR: 148.22, 146.17, 144.28, 142.44, 139.24, 129.37, 128.24, 127.95, 127.78, 127.42, 126.13, 121.73, 119.35, 114.10, 109.79, 95.61, 84.06, 55.99, 34.43, 33.79, 29.42, 29.36, 29.21, 29.09, 28.90, 23.54.

c) Synthesis of 2-(hydroxydiphenylmethyl)-4-methoxyphenol

A solution of bromobenzene (23.55 g, 150 mmol) in ether (70 mL) was added dropwise during 1.2 h to a suspension of magnesium turnings (4.37 g, 180 mmol) in ether (5 mL). The reaction mixture was heated under reflux for 1 h. After cooling to room temperature, 5-methoxysalicylic acid (3.03 g, 18 mmol) in ether (70 mL) was added dropwise during 45 min, and the reaction mixture was left stirring at room temperature overnight. The reaction mixture was decanted and cooled on an ice-bath, before HCl (10%) was added. Extraction with ether (2×), washing with water (2×) and drying (Na$_2$SO$_4$) afforded the crude product. Filtration and washing with cold ethyl acetate and re-crystallizing the filtrate finally gave 3.17 g (58%) of the target compound.

$^1$H-NMR: 7.60 (s, 1H), 7.35-7.28 (m, 6H), 7.23-7.18 (m, 4H), 6.79 (d, 1H), 6.74 (dd, 1H), 6.10 (d, 1H), 3.86 (s, 1H), 3.58 (s, 3H).

$^{13}$C-NMR: 152.14, 149.73, 144.73, 131.17, 128.17, 127.92, 127.73, 117.89, 116.57, 113.78, 84.11, 55.58.

Synthesis of (±)-2-(9-decenyl)-6-methoxy-4,4-diphenyl-4H-benzo[d][1,3]dioxine

A mixture of 2-(hydroxydiphenylmethyl)-4-methoxyphenol (1.00 g, 3.3 mmol), 10-undecenal (0.37 g, 2.2 mmol) and 4-methylbenzenesulfonic acid hydrate (0.04 g, 0.2 mmol) in toluene (11 mL) was stirred at room temperature for 72 h. The reaction mixture was concentrated. Flash chromatography (SiO$_2$, heptane/ethyl acetate 7:1) gave 1.01 g (quant.) of the target compound.

$^1$H-NMR: 7.39-7.30 (m, 5H), 7.27-7.17 (m, 5H), 6.84 (d, 1H), 6.74 (dd, 1H), 6.36 (d, 1H), 5.85-5.75 (m, 1H), 5.01-4.95 (m, 1H), 4.95-4.90 (m, 2H), 3.62 (s, 3H), 2.06-1.99 (m, 2H), 1.89-1.74 (m, 2H), 1.52-1.31 (m, 4H), 1.31-1.13 (m, 8H).

$^{13}$C-NMR: 152.77, 146.65, 146.13, 144.30, 139.21, 129.23, 128.11, 127.98, 127.92, 127.84, 127.43, 125.92, 117.55, 115.03, 114.11, 114.02, 95.16, 84.12, 55.56, 34.46, 33.79, 29.43, 29.36, 29.29, 29.09, 28.90, 23.44.

Example 4

Dynamic Headspace Analysis of the Release of a Perfuming Ingredient from the Invention's Photosensitive Acetal or Ketal Derivatives Incorporated into a Consumer Product (Fabric Softener)

A fabric softener base with the following final composition has been prepared:

| | |
|---|---|
| Stepantex ® VL90 A (origin: Stepan) | 16.5% by weight |
| Calcium chloride (10% aq. solution) | 0.6% by weight |
| Water | 82.9% by weight |

In a beaker, a solution of one of the photosensitive acetal or ketal derivative described in Examples 2 and 3 (0.026 mmol) in acetone (0.2 mL) was added to the fabric softener (1.8 g). After homogenization, the sample was dispersed with 600 mL of demineralized cold tap water. One cotton sheet (EMPA cotton test cloth Nr. 221, origin: Eidgenössische Materialprifanstalt), pre-washed with an unperfumed detergent powder and cut to ca. 12×12 cm sheets) was added and agitated manually for 3 min, left standing for 2 min, then wrung out by hand, and weighed to obtain a constant quantity of residual water. A reference sample consisting of an equimolar amount of the corresponding aldehyde or ketone to be released (0.026 mmol) in acetone (0.2 mL) was added to the fabric softener (1.8 g) and analyzed the same way. The cotton sheets (one with the photosensitive acetal or ketal derivative and one with the corresponding fragrance to be released) were line-dried for 24 h in the dark. The cotton sheets were then analyzed. For the measurements, the sheets with the photosensitive acetal or ketal derivative were put into a headspace sampling cell (ca. 160 mL inner volume) and exposed to a xenon lamp (Heraeus Suntest CPS at about 90000 lux), which served as a sunlight simulator, whereas the sheet with the free fragrance was put into the headspace sampling cell exposed to natural indoor daylight. The headspace sampling cells were thermostatted at 25° C. and exposed to a constant air flow of ca. 200 mL/min. The air was filtered through active charcoal and aspirated through a saturated solution of NaCl (to ensure a constant humidity of the air of ca. 75%). The system was equilibrated during 15 min while adsorbing the volatiles on a waste cartridge. Then, six times consecutively, the volatiles were adsorbed for 10 min on a clean cartridge and 20 min on a waste cartridge. The waste cartridges were discarded; the other cartridges were desorbed on a Perkin Elmer TurboMatrix ATD desorber coupled to an Agilent Technologies 7890A gas chromatograph equipped with a HP-1 capillary column (30 m, i.d. 0.32 mm, film 0.25 μm) and a FID detector. The volatiles were analyzed using a temperature gradient starting at 70° C. for 1 min, then going to 220° C. at 10° C./min. Headspace concentrations (in ng/L air) were obtained by external standard calibrations using five different concentrations of the fragrance to be released in ethanol. Each calibration solution (0.1 μL) was injected onto a clean Tenax® cartridge, which was desorbed and analyzed under the same conditions. The results obtained for the release of the different fragrances are summarized in Table 1. All values are average values of at least two measurements.

TABLE 1

Headspace concentrations of fragrance aldehydes or ketones released from photolabile acetal or ketal derivatives according to the invention on cotton upon exposure to a xenon lamp as compared to the corresponding reference sample measured after sampling for 55 min (=data from second of the six samplings described above)

| Compound of formula (I) from | Name and headspace concentration of fragrance released upon exposure to xenon lamp [ng/L] | Headspace concentration of reference [ng/L] | Approx. factor of increase |
| --- | --- | --- | --- |
| Example 2a | 10-Undecenal | 837.1 | 5.5 | 150 |
| Example 2e | 10-Undecenal | 403.1 | 5.5 | 70 |
| Example 2f | 10-Undecenal | 520.0 | 5.5 | 90 |
| Example 2g | 10-Undecenal | 477.0 | 5.5 | 90 |
| Example 2h | 10-Undecenal | 20.9 | 5.5 | 4 |
| Example 2i | 10-Undecenal | 117.3 | 5.5 | 20 |
| Example 3a | 10-Undecenal | 4.3 | 5.5 | 1 |
| Example 3b | 10-Undecenal | 2.5 | 5.5 | 0.5 |
| Example 3c | 10-Undecenal | 6.9 | 5.5 | 1 |
| Example 2b | Methoxymelonal | 342.9 | 1.7 | 200 |
| Example 2c | Trifernal ® | 159.4 | 2.9 | 50 |
| Example 2d | 3,5,5-Trimethylhexanal | 579.5 | 2.8 | 210 |

The data show that all photosensitive compounds of formula (I) prepared as described in Examples 2 and 3 released the corresponding fragrance upon exposure to light from a fabric softener application. While the compounds from Example 3 (with all $R^4$ and $R^5$ being hydrogen atoms) released 10-undecenal in the same order of magnitude as the reference sample, exposure of the compounds from Example 2 (with one $R^4$ and $R^5$ not being a hydrogen atom) to the xenon lamp resulted in significantly higher headspace concentrations than the reference. It is thus advantageous that at least one of the substituents $R^4$ and $R^5$ in the compound of formula (I) is not a hydrogen atom.

Please note that performing the headspace measurements after drying for only 24 h is favorable for the reference sample consisting of the corresponding unmodified aldehyde or ketone. After the fabric softening process, the unmodified aldehydes and ketones start evaporating from the cotton surface, and the more time has passed the more the compounds had time to evaporate. However, the invention's photosensitive acetal or ketal derivatives are non-volatile and release the corresponding fragrance aldehydes and ketones only on exposure to light, independent of the time of drying. The approx. factors of increase reported in Table 1 are thus expected to increase if the headspace sampling was carried out after 3 days or after 7 days.

What is claimed is:

1. A delivery system for releasing one or more active volatile aldehydes or ketones comprising a compound of formula

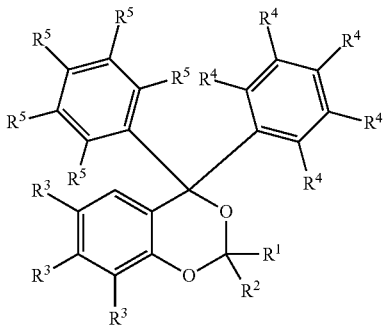

wherein
$R^1$ and $R^2$ represent simultaneously or independently a hydrogen atom, a $C_{1-18}$ hydrocarbon group or a $C_{1-18}$ group that includes one to three oxygen atoms, one to two nitrogen atoms, and/or one sulfur atom, provided that at least one or both of $R^1$ and $R^2$ includes one of the $C_{1-18}$ groups; wherein $R^1$ and $R^2$ are derived from an active aldehyde or ketone of formula $(R^1)(R^2)C(=O)$; said aldehyde or ketone having a molecular weight comprised between 80 and 230 g/mol and being a $C_{5-18}$ compound;

$R^3$ represent simultaneously or independently from each other, a hydrogen atom, a linear $C_1$-$C_8$ alkyl group, a branched or cyclic $C_3$-$C_8$ alkyl group, a hydroxy group, a methoxy group, an ethoxy group, a 2-hydroxyethoxy group, a 2-ethoxyethoxy group, a $(OCH_2CH_2)_nOH$ group, a $(OCH_2CH_2)_nOCH_3$ group, a methylthio group, a dimethylamino group, or a diethylamino group, with n being an integer varying between 2 and 8; and $R^4$ and $R^5$ represent, simultaneously or independently from each other, a hydrogen atom, a linear $C_1$-$C_4$ alkyl group, a branched $C_3$-$C_4$ alkyl group, a methoxy group, an ethoxy group, a 2-hydroxyethoxy group, a 2-ethoxyethoxy group, a $(OCH_2CH_2)_nOH$ group, a $(OCH_2CH_2)_nOCH_3$ group, a methylthio group, a dimethylamino group, or a diethylamino group, with n having the same meaning as above, wherein at least one $R^4$ and at least one $R^5$ are a dimethylamino group.

2. The delivery system of claim 1, wherein at least two $R^4$ and/or at least two $R^5$ are hydrogen atoms.

3. The delivery system of claim 1, wherein all of the groups $R^4$ and $R^5$, which are not a hydrogen atom, represent the same group.

4. The delivery system of claim 1, wherein the $R^4$ and $R^5$ group in ortho position with respect to the bond between the aromatic ring and the oxygenated ring are hydrogen atoms.

5. The delivery system of claim 1, wherein $R^4$ and $R^5$ are a hydrogen atom, a methoxy group or the dimethylamino group.

6. The delivery system of claim 1, wherein $R^3$ represents a hydrogen atom, a linear or branched $C_1$-$C_4$ alkyl group, a methoxy group, a dimethylamino group or a diethylamino group.

7. The delivery system of claim 1, wherein the active volatile aldehyde or ketone is a perfuming ingredient.

8. The delivery system of claim 7, wherein the release of the perfuming compounds, is triggered by light at a wavelength above 280, above 300 nm, or above 330 nm.

9. A perfuming composition comprising
i) at least one compound of formula (I), as defined in claim 1;

ii) at least one ingredient selected from the group consisting of a perfumery carrier and a perfumery base; and iii) optionally at least one perfumery adjuvant.

10. A perfuming consumer product comprising at least one compound of formula (I), as defined in claim 1.

11. The perfuming consumer product of claim 10, wherein the perfumery consumer product is a perfume, a fabric care product, a body-care product, an air care product, a home care product or a car care product.

12. The perfuming consumer product of claim 10, wherein the perfumery consumer product is a fine perfume, a cologne, an after-shave lotion, a liquid or solid detergent, a unidose detergent, a fabric softener, a fabric refresher, an ironing water, a paper, a bleach, a carpet cleaner, a curtain-care product, a shampoo, a conditioner, a coloring preparation, a color care product, a hair shaping product, a hair spray, a skin cream or lotion, a vanishing cream, a deodorant or antiperspirant, a perfumed soap, shower or bath mousse, oil or gel, a hygiene product, an air freshener, a "ready to use" powdered air freshener, a wipe, a dish detergent, a leather care product, a hard-surface detergent, a polish, a wax or a plastic cleaner.

13. An acetal or ketal compound of formula

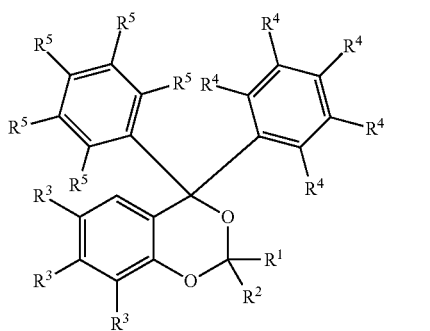

(I)

wherein $R^1$ and $R^2$, simultaneously or independently, represent a hydrogen atom, a $C_{1-18}$ hydrocarbon group, or a $C_{1-18}$ group that includes one to three oxygen atoms, one to two nitrogen atoms, and/or one sulfur atom, provided that at least one or both of $R^1$ and $R^2$ includes one of the $C_{1-18}$ groups; wherein $R^1$ and $R^2$ are and derived from an active aldehyde or ketone of formula $(R^1)(R^2)C(=O)$; said aldehyde or ketone having a molecular weight comprised between 80 and 230 g/mol and being a $C_{5-18}$ compound;

$R^3$ represent simultaneously or independently from each other, a hydrogen atom, a linear $C_1$-$C_8$ alkyl group, a branched or cyclic $C_3$-$C_8$ alkyl group, a hydroxy group, a methoxy group, an ethoxy group, a 2-hydroxyethoxy group, a 2-ethoxyethoxy group, a $(OCH_2CH_2)_nOH$ group, a $(OCH_2CH_2)_nOCH_3$ group, a methylthio group, a dimethylamino group, or a diethylamino group, with n being an integer varying between 2 and 8;

$R^4$ and $R^5$ represent, simultaneously or independently, from each other, a hydrogen atom, or a methylthio group, with at least one $R^4$ or $R^5$ being a methylthio group.

14. The compound of claim 13, wherein the $R^4$ and $R^5$ groups in ortho position with respect to the bond between the aromatic ring and the oxygenated ring are hydrogen atoms, or wherein the $R^4$ and $R^5$ groups in ortho and para position with respect to the bond between the aromatic ring and the oxygenated ring are hydrogen atoms.

15. The delivery system of claim 1, wherein $R^1$ is a $C_{5-18}$ group and each $R^3$ is H.

16. The delivery system of claim 1, wherein, in the compound of formula (I), $R^1$ is $C_{10}H_{19}$, $R^2$ is H, each $R^3$ is H, one $R^4$ is $N(CH_3)_2$ while the other $R^4$s are H, and one $R^5$ is $N(CH_3)_2$ while the other $R^5$s are H.

17. A perfuming composition comprising
i) at least one compound of formula (I), as defined in claim 13;
ii) at least one ingredient selected from the group consisting of a perfumery carrier and a perfumery base; and
iii) optionally at least one perfumery adjuvant.

18. A perfuming consumer product comprising at least one compound of formula (I), as defined in claim 13.

19. The perfuming consumer product of claim 18, wherein the perfumery consumer product is a perfume, a fabric care product, a body-care product, an air care product, a home care product or a car care product.

20. The perfuming consumer product of claim 18, wherein the perfumery consumer product is a fine perfume, a cologne, an after-shave lotion, a liquid or solid detergent, a unidose detergent, a fabric softener, a fabric refresher, an ironing water, a paper, a bleach, a carpet cleaner, a curtain-care product, a shampoo, a conditioner, a coloring preparation, a color care product, a hair shaping product, a hair spray, a skin cream or lotion, a vanishing cream, a deodorant or antiperspirant, a perfumed soap, shower or bath mousse, oil or gel, a hygiene product, an air freshener, a "ready to use" powdered air freshener, a wipe, a dish detergent, a leather care product, a hard-surface detergent, a polish, a wax or a plastic cleaner.

* * * * *